(12) United States Patent
Wang (10) Patent No.: US 7,204,812 B2
(45) Date of Patent: Apr. 17, 2007

(54) TRANSENDOSCOPIC NEEDLE ASSEMBLY

(76) Inventor: Ko-Pen Wang, 14525 Falls Rd., Butler, MD (US) 21023

( * ) Notice: Subject to any disclaimer, the term of this patent is extended or adjusted under 35 U.S.C. 154(b) by 321 days.

(21) Appl. No.: 10/693,646

(22) Filed: Oct. 27, 2003

(65) Prior Publication Data

US 2005/0090764 A1 Apr. 28, 2005

(51) Int. Cl.
*A61B 10/00* (2006.01)
*A61B 17/32* (2006.01)

(52) U.S. Cl. .................. 600/566; 600/564; 606/170

(58) Field of Classification Search ............... 600/562, 600/564–567; 606/167, 170
See application file for complete search history.

(56) References Cited

U.S. PATENT DOCUMENTS

| | | | |
|---|---|---|---|
| 4,249,541 A | | 2/1981 | Pratt |
| 4,329,980 A | * | 5/1982 | Terada .................. 600/144 |
| 4,532,935 A | | 8/1985 | Wang |
| 4,617,940 A | | 10/1986 | Wang |
| 4,693,257 A | * | 9/1987 | Markham .................. 600/565 |
| 4,702,260 A | | 10/1987 | Wang |
| 4,766,906 A | | 8/1988 | Wang |
| 4,791,937 A | | 12/1988 | Wang |
| 4,890,626 A | | 1/1990 | Wang |
| 4,966,162 A | | 10/1990 | Wang |
| 5,041,082 A | * | 8/1991 | Shiber .................. 604/22 |
| 5,056,529 A | * | 10/1991 | de Groot .................. 600/567 |
| 5,320,110 A | | 6/1994 | Wang |
| 5,601,588 A | * | 2/1997 | Tonomura et al. .......... 606/185 |
| 2005/0090763 A1 | * | 4/2005 | Wang .................. 600/564 |

* cited by examiner

*Primary Examiner*—Max Hindenburg
*Assistant Examiner*—Michael Apanius
(74) *Attorney, Agent, or Firm*—Davidson Berquist Jackson & Gowdey, LLP (57) ABSTRACT

A medical device for obtaining biopsy tissue samples is provided. The device includes a flexible outer tubular member having proximal and distal ends, and a flexible inner member slidably and preferably coaxially received within the outer tubular member. The inner member includes a flexible member adjacent the proximal end of the outer tubular member, a first spring section having proximal and distal ends and being oriented adjacent the distal end of the outer tubular member, and a second spring section therebetween. A retractable hollow needle member or other specimen collection device is coupled to the distal end of the first spring section. The device has a retracted position wherein the needle member is retractably housed within the outer tubular member, a first extended position wherein the needle member is at least partially deployed beyond the distal end of the outer tubular member and the second spring section is in an uncompressed state, and a second extended position wherein the second spring section is in a compressed state.

21 Claims, 5 Drawing Sheets

TRANSENDOSCOPIC NEEDLE ASSEMBLY

FIELD OF THE INVENTION

This invention relates generally to a transendoscopic needle assembly for use with a flexible bronchoscope, endoscope or any other type of body cavity scope, and more particularly to an improved transendoscopic needle assembly and operating mechanism for obtaining tissue samples from within the body.

BACKGROUND OF THE INVENTION

Conventionally, when biopsies were desired to be taken of the lymph nodes, for example, so as to aid in the diagnosis of carcinoma, the prior techniques would all typically utilize a substantially rigid needle and penetrate the body via percutaneous entry. For example, U.S. Pat. Nos. 3,630,192 and 3,628,524 each to Jamshidi disclose biopsy needles suitable for percutaneous entry. More recently, less invasive flexible biopsy instruments which do not require percutaneous entry have been described. U.S. Pat. No. 4,249,541 to Pratt discloses that a flexible biopsy instrument can be utilized in combination with a fiberoptic bronchoscope.

U.S. Pat. No. 4,617,940 to Wang, the entirety of which is incorporated herein by reference, describes a completely flexible bronchoscopic needle assembly wherein relatively non-invasive biopsy procedures can be performed utilizing a needle in combination with a fiberoptic bronchoscope. The attending physician inserts the bronchoscope into a predetermined one of the patient's natural orifices, or other site, depending upon the particular portion of the body one desires to obtain a sample of tissue to be biopsied. The needle assembly, which includes an outer catheter and an inner coaxial stylet attached to a retractable needle, is slideably inserted into a receiving passageway of the bronchoscope. The needle, directly connected to the proximal end by a stiff wire, is urged into the tissue of the patient by a stabbing force exerted on the proximal end of the stylet (e.g. the end on the exterior of the patient's body) after the outer catheter comes into the bronchoscope's field of view. The bronchoscope enables the attending physician to accurately position the needle and to penetrate the exact location of the desired tissue area due to the viewing capabilities provided thereby.

A particular problem in utilizing a flexible bronchoscopic needle is that the needle assembly must be flexible enough to allow the physician to maneuver the assembly to the target site, but yet rigid enough to allow penetration of the needle into the target tissue. The bronchial wall or hard tumor tissue will frequently need to be penetrated and may present significant resistance to entry of the needle. Thus, upon arrival to the target site, the needle assembly, particularly the distal portion of the needle assembly, needs flexibility to directionally maneuver around bends and curves, yet also needs to be rigid enough to provide a countering pressure against the resistance provided by the bronchial wall or hard tumor tissue. Conventional flexible needle assemblies have not provided satisfactory means for balancing the necessary flexibility with the desired rigidity as the needle is directed toward the target tissue. Thus, a need exists for a needle assembly having flexible characteristics as the assembly is maneuvered through a scope or other device while also having rigid characteristics as the needle is inserted into the target tissue.

SUMMARY OF THE INVENTION

The present invention is directed to a medical device for obtaining biopsy tissue samples. The device includes a flexible outer tubular member having proximal and distal ends, and a flexible inner member slidably and coaxially received within the outer tubular member. The inner member includes a flexible stylet adjacent the proximal end of the outer tubular member, a first spring section having proximal and distal ends and being oriented adjacent the distal end of the outer tubular member, and a second spring section coupled to the stylet and the proximal end of the first spring section. A retractable hollow needle member comprising a hollow needle is coupled to the distal end of the first spring section. The device has a retracted position, wherein the needle member is retractably housed within the outer tubular member, a first extended position wherein the needle member is at least partially deployed beyond the distal end of the outer tubular member and wherein the second spring section is in an uncompressed state, and a second extended position wherein needle member is at least partially deployed and wherein the second spring section is in a compressed state.

Optionally, the device also includes a hard tip fixed to the distal end of the outer tubular member, the tip including a bearing surface on the proximal end thereof. The needle member comprises a hollow needle and a limiting member rigidly associated with the needle and contacting the bearing surface of the tip member in the first and second extended positions. Preferably, the first spring section comprises a first wavelength and the second spring section comprises a second wavelength different from (greater than or less than) the first wavelength in the retracted and first extended positions. The second spring section has a third wavelength in the second extended position, the third wavelength being less than the second wavelength. Preferably, the stylet passes into and through an inner volume defined by the second spring section whether the device is in the retracted, the first or the second extended positions. Similarly, the stylet preferably passes into the inner volume defined by the first spring section in the retracted and first extended positions, and passes through the inner volume thereof in the second extended position. Optionally, the stylet extends into the needle in the second extended position in order to provide increased rigidity.

A biasing member optionally is provided which biases the inner member into a contacting relationship with the bearing surface to prevent retractable movement of the needle member when in the second extended position. Similarly, the inner member may comprise a biasing member biasing the inner member into a contacting relationship with a second bearing surface to prevent retractable movement of the needle member when in the retracted position. The second bearing surface preferably is adjacent the proximal end of the outer tubular member.

In another embodiment, the invention is directed to a tissue collection device including an elongated outer flexible hollow catheter having proximal and distal ends. An elongated member is slidably positioned within the hollow catheter and defines an axis along its length. A helically wound wire member having proximal and distal ends is coaxially attached to the elongated member, wherein the wire member has a proximal region having a first wavelength, and a distal region having a second wavelength normally smaller than the first wavelength. A sampling device, e.g., a hollow needle, is attached to the distal end of the helically wound wire member. The device preferably includes a first extended position wherein the sampling device extends beyond the distal end of the catheter, and a second extended position wherein the sampling device extends beyond the distal end of the catheter and the proximal region has a compressed wavelength shorter than the first wavelength.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE INVENTION

The present invention is directed to a medical device, which includes a flexible outer tubular member, e.g., a flexible catheter, having proximal and distal ends. As used herein, the proximal end of a component of the medical device is the end closest to the administering physician during normal use, and the distal end is the end of the component farthest away from the administering physician, e.g., the end closest to the target site, during normal operation. A flexible inner member is slidably and coaxially received within the outer tubular member. The inner member includes a flexible member, e.g., a flexible stylet, housed within the proximal end of the outer tubular member; a first spring member or section having proximal and distal ends and being oriented adjacent the distal end of the outer tubular member; and a second spring member or section oriented between the stylet and the first spring section. A retractable hollow needle member is coupled to the distal end of the first spring section. The device has a retracted position wherein the needle member is retractably housed within the outer tubular member; a first extended position wherein the needle member is at least partially deployed beyond the distal end of the outer tubular member, and wherein the second spring section is in an uncompressed state; and a second extended position wherein the needle member is at least partially deployed and wherein the second spring section is in a compressed state. The medical device is particularly suited for use with an endoscope. The device can be inserted into a patient's orifice and flexibly directed to a target site, e.g., a tumor, within the patient's body. Once at the target site, the needle in the medical device can be extended to pierce the target site in order to obtain a biopsy and/or fluid sample from the target site. The second extended position provides a substantially rigid distal end region in the medical device whereby effective penetration of the target site can be readily achieved.

Figure 1:
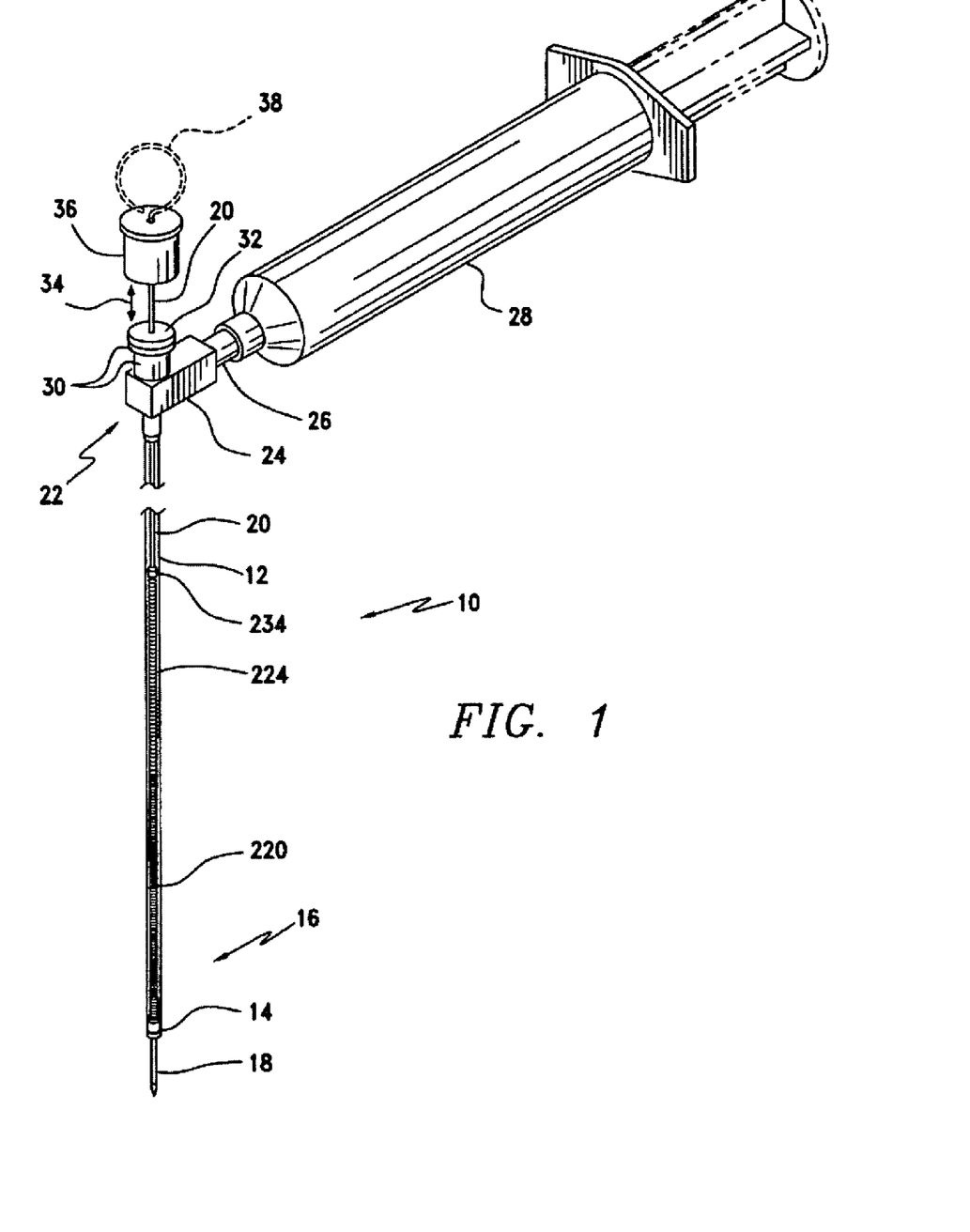
FIG. 1 is a representative perspective view of the biopsy needle assembly in accordance with the present invention.

FIG. 1 is representative of one exemplary embodiment of the present invention. As shown in FIG. 1, the biopsy collection assembly 10 generally includes an outer catheter 12, a metal tip 14 fixed to the distal end 16 of catheter 12, and a specimen collection member such as, for example, a rigid hollow needle 18 coaxial with tip 14. In addition to hollow needle 18, the specimen collection device could include a brush, a spoon-shaped needle, a needle with a variety of end configurations or an open side wall in which tissue could be harvested for subsequent study. A flexible stylet 20 is slideably received within catheter 12 for a purpose which will become clearer from the discussion below. The distal end 16 also preferably includes first and second spring sections, 220 and 224, respectively, which are described in more detail with reference to FIGS. 2–4. The proximal end of the second spring section 224 is securely attached to the stylet 20 with a coupling member 234.

The proximal end 22 of assembly 10 preferably includes a conventional two-directional leur lock 24. One of the two directional nipples 26 can accept an aspirating device, e.g., a conventional syringe 28, while the other directional nipple 30 is coaxially positioned relative to catheter 12. An elastomeric seal 32, through which stylet 20 passes, preferably covers nipple 30. Seal 32 is provided so as to permit all suction forces generated by syringe 28 to be communicated through catheter 12 and needle 18 when it is desired to obtain biopsy tissue samples. Thus, no fluid leakage will occur in the vicinity of stylet 20 where it passes through seal 32 yet reciprocal movement (arrow 34) of stylet 20 is permitted. Aspiration is effected through an annular space through which biopsy material can flow, wherein the annular space is the region between the interior cavity of catheter 12 and stylet 20. A grippable cap 36 is fixed to the proximal end of stylet 20 so as to permit the attending physician to effect reciprocal movement of each. Additionally or alternatively, a finger ring, shown in phantom at 38, may be provided to allow the physician to extend and retract the needle device with a single hand. A portion of the stylet may be adapted to pass through the grippable cap and form the finger ring.

The needle assembly of the present invention is particularly well suited for use in combination with a flexible fiberoptic bronchoscope. As used herein and in the appended claims, the term "flexible" is meant to refer to axial flexion through an arc of 360 degrees, e.g., axially looped. Thus, such flexibility permits the needle assembly to negotiate sharp turns, even to the extent of permitting U-turns thereof.

In order to permit such flexibility, catheter 12 is preferably constructed of a durable plastic or other synthetic material. Similarly, stylet 20 can be constructed of fine gauge metal or plastic wire, the flexibility thereof being substantially equal to the flexibility of the catheter 12 in which it is slideably received.

Figure 2:
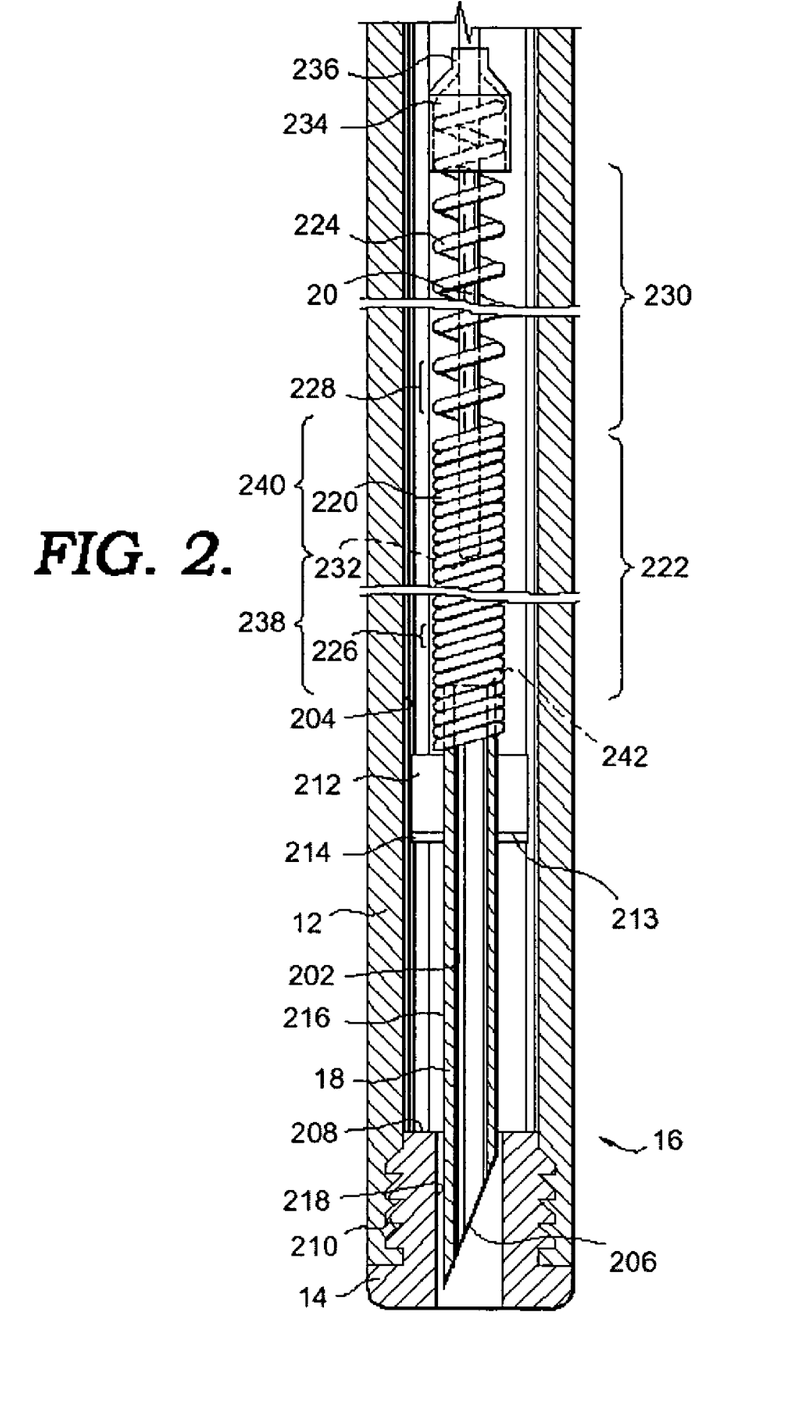
FIG. 2 is a detailed partial cross-sectional view of the distal end of the biopsy needle assembly of the present invention in the retracted position.
Figure 3:
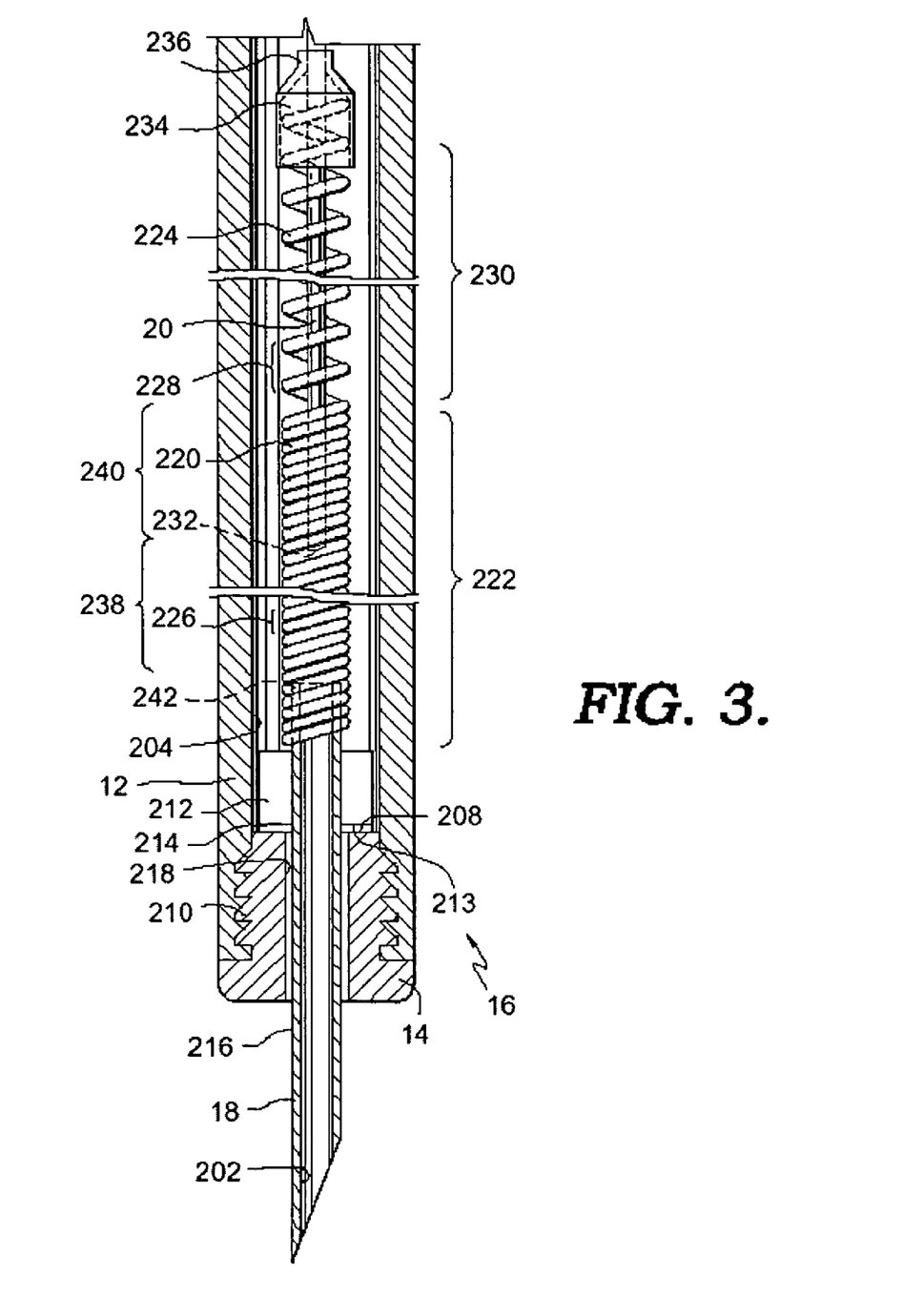
FIG. 3 is a detailed partial cross-sectional view of the distal end of the biopsy needle assembly of the present invention in a first extended position.
Figure 4:
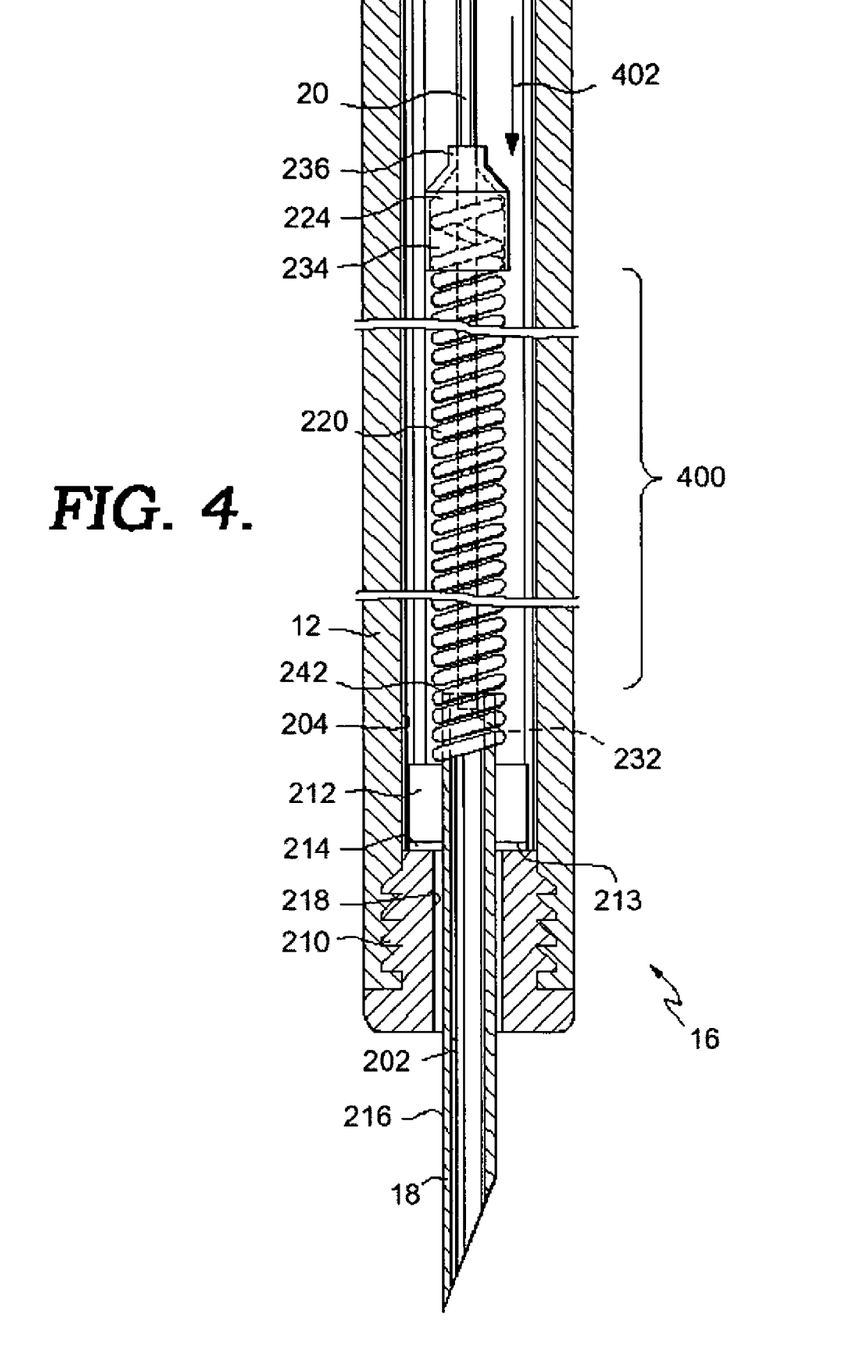
FIG. 4 is a detailed partial cross-sectional view of the distal end of the biopsy needle assembly of the present invention in a second extended position.

In operation, the flexible medical device of the present invention is directed through a patient's orifice while the needle 18 is in a retracted position, illustrated in FIG. 2. In the retracted position, the needle 18 is completely housed within tip 14 and catheter 12, and the second spring section 224 is uncompressed. Once the tip 14 of the medical device has traversed the patient's orifice and has been directed to the desired target site, the administering physician moves the grippable cap 36 distally to transform the medical device from the retracted position to a first extended position, which is illustrated in FIG. 3. In the first extended position, the needle 18 extends beyond the tip 14 and the first spring section 224 remains uncompressed. When penetration of the target site is desired, the physician moves the grippable cap 36 distally further to transform the medical device from the first extended position to the second extended position, which is illustrated in FIG. 4.

The grippable cap 36 optionally is lockingly engaged with directional nipple 30 while in the second extended position in order to allow the administering physician to maintain the device in the second extended position without physically exerting continuous pressure on grippable cap 36. In the second extended position, the needle 18 extends beyond the tip 14 and the second spring section 224 is in a compressed state and exhibits desirably rigid characteristics for penetrating the target site.

Optionally, while in the first and/or the second extended positions, the needle 18 is reciprocally moved in a back and forth manner by manipulating the grippable cap 36 and/or by moving the leur lock 24 in a back and forth manner. By so doing, fluid or tissue samples can be sheared away from the target site. Thereafter, the grippable cap 36 is unlocked from directional nipple 30 (if it was lockingly engaged with directional nipple 30) and is moved proximally to transform the medical device from the second extended position to the first extended position.

While in the first and/or second extended positions, aspiration optionally is performed, e.g., with syringe 28, in order to obtain a liquid or tissue sample within one or more of needle 18, catheter 12, first spring section 220 and/or second spring section 224. After a sample has been obtained, the grippable cap 36 is further moved in the proximal direction in order to transform the medical device to a retracted position, and the device (which houses the biopsy sample) is removed from the patient's orifice.

FIG. 2 illustrates the distal end 16 of an exemplary medical device in a retracted position according to the present invention. As shown, tubular needle 18 forms an inner surface 202, which defines a needle cavity within the needle 18. The needle cavity is in communication with an interior cavity, which is defined by inner surface 204 of catheter 12. The interior cavity is preferably substantially cylindrical throughout its entire length although the flexibility of the device can provide for deviations from a cylindrical form. The needle cavity is substantially coaxially situated within the interior cavity, the diameter of the former being preferably about one-third to about one-half that of the latter. Stylet 20, on the other hand, optionally is sized so as to be closely received within the needle cavity. Thus, stylet 20 preferably is similarly about one-third to about one-half the diameter of the needle cavity so as to establish a significant annular space through which biopsy tissue and/or fluids can easily flow.

The distal end of needle 18 defines a sharp edge 206 for penetrating a patient's tissue while in an extended position (see FIG. 4) to obtain samples thereof. The proximal end 242 of needle 18 is attached to a first spring section 220, as described in more detail below. It should be understood, that while the tip of the outer hollow needle 18 has been shown as being pointed and sharpened in a conventional way, the needle could also have a more circular outer end, or an outer tip that has been sharpened in any other manner that would accomplish the desired purpose of collecting tissue specimens. Alternatively, a brush may be implemented in the present invention in lieu of a needle, as described by my U.S. Pat. No. 4,966,162, previously referenced.

Needle 18 also includes a fixed hub 212, which preferably encircles the needle 18 adjacent the proximal end thereof. The hub 212 may be attached to the needle with an adhesive, solder, by being formed there-around or by mechanical means, e.g., crimping. The hub 212 includes a distally-facing surface 213 which is biasable against proximal end 208 of tip 14 when the medical device is in the first or second extended position. In this manner, as the needle is extended, the distal movement of the needle 18 will be ultimately limited as the distally-facing surface 213 of the hub 212 contacts proximal end 208 of tip 14. Hub 212 preferably is constructed of a hard material such as stainless steel, plastics, or the like.

Optionally, as shown in FIGS. 2–4, a pliable O-ring 214 is fixedly or removably oriented against the distally-facing surface 213 of hub 212. When the needle is in an extended position, the O-ring provides a seal between the distally facing surface 213 of hub 212 and the proximal end 208 of tip 14. This seal advantageously prevents fluid or biopsy tissue from between outer surface 216 of needle 18 and inner surface 218 of metal tip 14 from entering the interior cavity. As a suction force is created by the aspirating device 28, a pressure drop is created within the interior cavity of catheter 12 and the needle cavity of needle 18 thereby facilitating the acquisition of biopsy tissue and/or fluid flow into and/or through the needle cavity. Optionally, the fluid or biopsy tissue flows through the needle 18 and into an inner cavity defined by the first spring section 220. The fluid or biopsy tissue also may flow into the inner cavity defined by the second spring section 224.

Preferably, after the needle has satisfactorily penetrated the target site, the leur lock is unlocked and the needle is placed in the first extended position by allowing the second spring section 224 to uncompress which partially retracts stylet 20 to the position shown in FIG. 3. While in the uncompressed state, gaps are provided between adjacent bends of the wire member defining the second wavelength 228 of second spring section 224. Suction applied at this point by the aspirating device will pull fluid or biopsy tissue into and through needle 18, into the inner cavity defined by the first spring section 220 and even perhaps into the inner cavity defined by the second spring section 224. The fluid or tissue then flows through the spaces or gaps between adjacent turns of the wire forming the second spring section 224 and into the interior cavity of the medical device. After the biopsy tissue or fluid has been sampled, the medical device is optionally placed in the retracted position and removed from the patient's body. The tissue or fluid can then be analyzed in order to diagnose the patient's ailment.

Tip 14 is an important feature of the present invention in that it effects secure union between needle 18 and catheter 12 thereby preventing deleterious separation thereof. Tip 14 is preferably constructed of a hard metal, e.g., stainless steel, or a hard plastic material. In accordance with the embodiment of FIG. 2, tip 14 is provided with a male threaded member 210 so that when threadingly inserted into the interior cavity, the male threaded member 210 acts as a tapping tool to cut corresponding female threads into the inner surface 204 of catheter 12. Thus, a self-tapping system is established whereby axial forces will be resisted in order to prevent separation of tip 14 and needle 18 from catheter 12. Additionally or alternatively, an adhesive is employed to secure the tip 14 to the catheter 12.

In accordance with the present invention, the proximal end 242 of needle 18 is securely attached to a first spring section 220 having proximal and distal ends. The first spring includes a plurality of turns of a wire member, with the distance between each turn defining a first wavelength 226. The distal end of first spring section 220 is preferably wrapped around and fixed to the proximal end 242 of needle 18. Preferably, the first spring section 220 is attached to the outer surface 216 of the proximal end 242 of needle 18, e.g., with an adhesive, solder, or simply by mechanical means. Because the first spring section 220 is fixedly secured at its distal end around needle 18, the first spring section 220 is also preferably coaxially and slidably oriented within outer catheter 12. Additionally or alternatively, a coupling member, not shown, may couple the distal end of the first spring section 220 to the outer surface 216 of the needle 18 adjacent the proximal end 242 thereof. The coupling member may be a tubular member including a first end crimped over the proximal end 242 of the needle 18 and a second end crimped over the distal end of the first spring section 220. Adhesive, solder or other mechanical means additionally or alternatively can be used to secure the coupling member to the needle and the first spring, thereby obtaining a secure union thereof. In another embodiment, not shown, the first spring section 220 is attached to the inner surface of needle 18 rather than the outer surface 216 thereof. In one embodiment, not shown, the proximal end of hub 212 may be adapted to receive the distal end of the first spring section 220. In this embodiment, the hub 212, which may be secured to the first spring by soldering, adhesive or mechanical means, e.g., crimping, acts as the coupling member.

The length of first spring section 220 defines a first region of flexibility 222 as shown in FIG. 2 which, in turn, has two additional sections 238 and 240. The first spring section 220 provides for increased flexibility in the first region 222 of the medical device of the present invention over conventional biopsy sampling devices. This increased flexibility provides significant advantages by allowing the distal end 16 of the medical device to be flexibly maneuvered through an endoscope or other similar instrument, or directly into a patient's orifice and to the target site to be sampled. The first region of flexibility 222 preferably includes two separated sections of flexibility while in the retracted position, as in FIG. 2 or the first extended position as in FIG. 3. In these positions, the distal end 232 of stylet 20 is located within the inner cavity defined by the first spring section 220. The stylet 20 provides slightly increased rigidity to a first section 240 of first region 222. However, because stylet 20 does not extend into the second section 238 of the first region 222, the second section 238 has particularly desirable more flexibility characteristics.

In the second extended position, the stylet 20 is extended to and preferably into the proximal end 242 of needle 18. Accordingly, in this position, the first region 222 has a consistent more rigid characteristic throughout its entire length. Preferably, in the second extended position, shown in FIG. 4, the rigidity in the spring region 400 between the proximal end 242 of needle 18 to the distal end of the coupling member 234 is relatively constant throughout its length because the second spring section 224 is ideally in a fully compressed state. However, in other embodiments, a slight deviation in rigidity may still exist in the first and second spring sections because of the inherent structural differences thereof.

The proximal end of first spring section 220 is preferably coupled to or integral with a second spring section 224 also having proximal and distal ends. The second spring section 224 includes a plurality of turns of a wire member, with the distance between each turn defining a second wavelength 228, which, in one embodiment, is larger than the first wavelength 226 while the medical device is in the retracted position. Alternatively, the second wavelength 228 is smaller than the first wavelength 226 while in the retracted position. Optionally, if first and second spring sections 220 and 224 are not integrally formed, the distal end of second spring section 224 is fixed to the proximal end of the first spring section 220 with an adhesive, solder, a coupling member, e.g., a tubular member crimped or otherwise secured about the first and second spring sections, or by other mechanical means. As shown in FIG. 2, the first and second springs are formed of a single wire member. That is, the first and second spring sections are integral with one another. Second spring section 224 is preferably oriented coaxially within outer catheter 12. The length of second spring section 224 defines a second region of flexibility 230 as shown in FIG. 2. The presence of the second spring section 224 with a different and greater wavelength than first spring section 220 provides for increased flexibility in the second region 230 of the medical device of the present invention over conventional biopsy sampling devices. Moreover, the mechanical properties of second spring section 224 are preferably such that the flexibility within the second region 230 is greater than the flexibility in the first region 222 while the needle is in the retracted position. This increased flexibility of these multiple springs provides significant advantages by allowing the distal end 16 of the medical device to flexibly maneuvered to the target site to be sampled.

As shown in FIG. 2, stylet 20 is preferably oriented coaxially within second spring section 224 and extends entirely therethrough whether the needle is retracted or extended. The proximal end of second spring section 224 is preferably fixedly attached to the stylet 20 with a coupling member 234. Coupling member 234, in one embodiment, is a substantially rigid sheath formed ideally of a metal or a metal alloy, e.g., stainless steel, although it could be formed from plastic or other moldable or machinable material. The coupling member 234 surrounds the proximal end of second spring section 224 and is secured thereto, e.g., with an adhesive, solder, or by mechanical means such as crimping. The coupling member 234 is also fixedly secured to the stylet 20 at the proximal end 236 of the coupling member, preferably by solder, adhesive, crimping or other mechanical means.

As the needle 18 and first and second spring sections, 220 and 224, are fixedly attached to the stylet 20 via coupling member 234, reciprocal movement of the stylet by an administering physician will move the first and second spring sections as well as the needle 18 reciprocally within and relative to catheter 12. In this manner, a physician may extend the needle 18 beyond tip 14 in preparation for obtaining a biopsy by distally moving the stylet 20 until the O-ring 214 contacts proximal end 208 of tip 14. The point of contact between the O-ring 214 and the proximal end 208 of tip 14 is designated a first extended position and is illustrated in FIG. 3. As additional pressure is asserted on the stylet 20 in the distal direction, the stylet will move distally causing the second spring section 224 to compress and increase its rigidity. Ideally, the length of the stylet 20 is such that as the second spring section 224 becomes fully compressed, the grippable cap 36, illustrated in FIG. 1, can be lockingly engaged via leur lock 24. This position, illustrated in FIG. 4, is designated herein as the second extended position. To ensure that distally-facing surface of hub 212 (or optional O-ring 214 associated therewith) securely bears against the proximal end 208 of tip 14 after progressing from the first extended position to the second extended position, a biasing force (arrow 402) is applied by stylet 20 which acts against coupling member 234, and thereby second spring section 224, first spring section 220 and needle 18, which is fixedly secured to hub 212. Secure locking engagement between internal threads (not shown) of cap 36 and one or more connection flanges on leur lock 24 maintains a biasing force as shown by arrow 402 without requiring manual retention of force by the attending physician. Thus, when stylet 20 is locked in the second extended position with the interaction between cap 36 and leur lock 24, compressed second spring section 224 applies a constant biasing force which is transferred through first spring section 220 and needle 18 to hub 212. In this manner, a biasing force of sufficient magnitude will be exerted against needle 18 to ensure that hub 212 or O-ring 214 bears against proximal end 208 of tip 14 thereby establishing rigid extension of needle 18 to prevent undesired retraction thereof.

This locking feature of the present invention ensures that the biasing force as shown by arrow 402 on needle 18 is provided so as to resist compression forces tending to retract or push needle 18 back into catheter 12. Resisting such compression forces is extremely important when consideration is given to the fact that oftentimes relatively tough tissue must be penetrated (e.g. bronchial walls or hard tumors) in order to obtain the desired biopsy material. Thus, such tough tissue may exert a sufficient amount of resistance against needle 18 so as to cause at least partial retraction thereof into outer catheter 12. Such partial retraction of needle 18 is to be strictly avoided in order to get the best sample in such hard tissue. For example, should partial retraction occur, the attending physician would not be able to completely penetrate the bronchial wall in order to obtain a biopsy sample of the lymph nodes therebehind. This inability may lead to a misdiagnosis of the patient's ailment, for example, as the tissue sample which will be obtained will not be of the diseased lymph node, but rather will be of the undiseased bronchial wall.

In another embodiment, the stylet 20 may interact with a recessed surface (not shown) which optionally is formed in the needle 18 by crimping a predetermined portion of needle 18 to reduce the diameter of the internal needle cavity at that point. The resulting narrowed flow path in needle 18 should be of sufficient diameter to permit biopsy material to pass therethrough. This interaction provides an additional biasing force further resisting undesired compression forces tending to retract needle 18 into catheter 12. The recessed surface embodiment is fully disclosed in my U.S. Pat. No. 4,617,940, the entirety of which is incorporated herein by reference.

When desired, needle 18 may simply be retracted by removing such biasing force, e.g., unlocking the leur lock, and proximally moving the stylet 20. The proximal motion of the stylet 20 first uncompresses the second spring section 224 to transform the medical device from the second extended position, illustrated in FIG. 4, to the first extended position, illustrated in FIG. 3. Upon further proximal movement of the stylet 20, the needle 18 is retracted into tip 14 and catheter 12, as shown in the retracted position illustrated in FIG. 2. While in the retracted position, the bronchoscope and patient can be protected from the needle 18 during introduction or removal of the medical device from the patient's orifice. Thus, the present invention protects the bronchoscope and patient from inadvertent tissue damage and/or needle damage, yet permits the attending physician to reliably perform the desired tissue biopsy.

By implementing the second spring section 224 in accordance with the present invention, the desired rigidity of the device when taking samples is not decreased. In the retracted and first extended positions, illustrated in FIGS. 2 and 3, respectively, the second spring is in an uncompressed and highly flexible state desirous for maneuvering the device through the patient's orifice. The overall flexibility of a structure including the spring plus an internal stylet will be much more flexible and thus more easily positioned within the patient. Surprisingly, when the second spring section 224 is in the second extended position, illustrated in FIG. 4, under compression and fully loaded with a limiting member such as the distally-facing surface of hub 212 or O-ring 214 in contact with proximal end 208 of tip 14, the needle 18 will be under rigid conditions able to withstand the repeated penetrations into tissue that are required in order to obtain the desired sampling within even dense or hard tissue areas.

Figure 5:
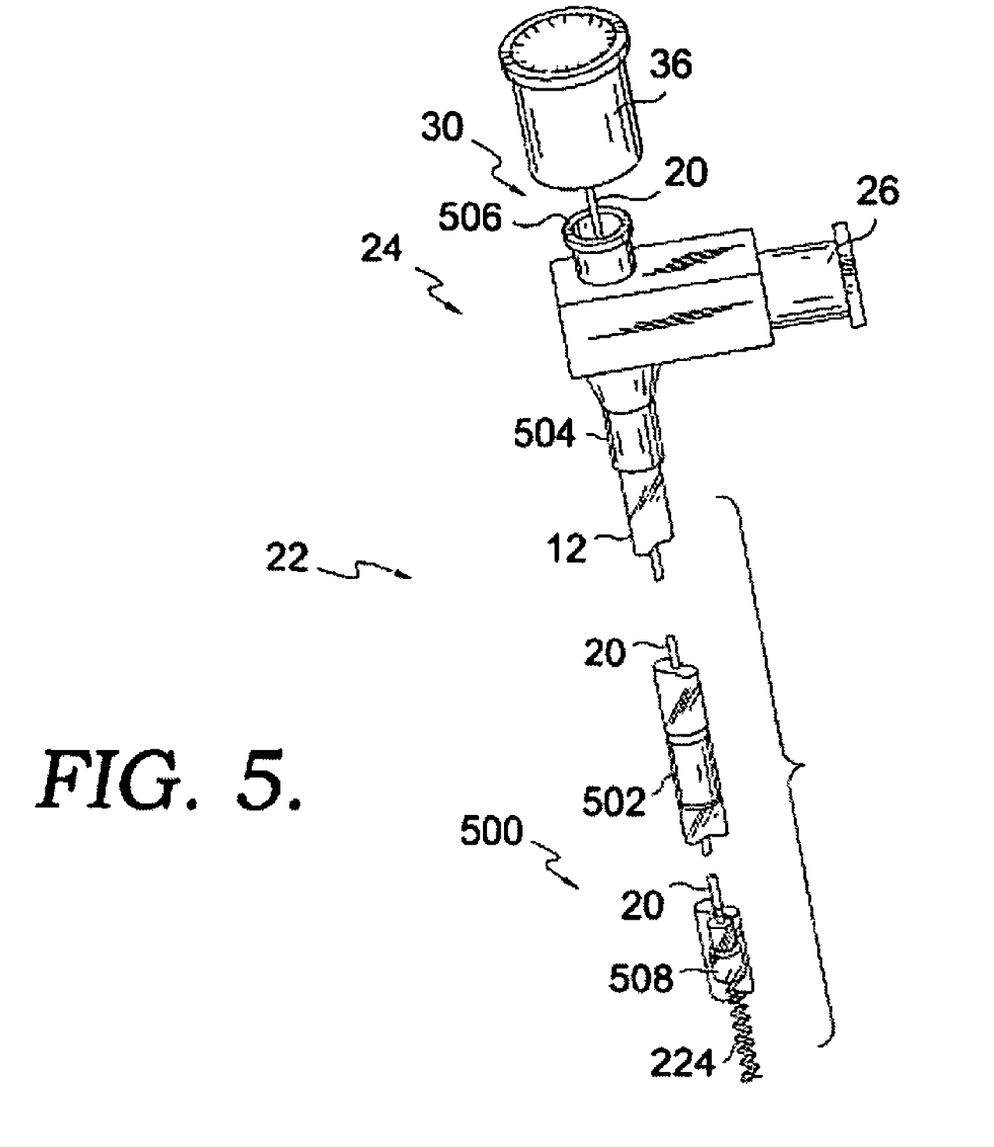
FIG. 5 is a perspective view of the proximal end of the present invention showing the stop member assembly.

FIG. 5 illustrates an embodiment of the proximal end 22 of the biopsy needle assembly 10 showing a stop member assembly 500 which desirably prevents separation of the stylet 20 from the catheter 12 and which also provides a guide for indicating to the administering physician that the needle 18 is in a fully retracted position. Leur lock 24 includes three connection members including a connection member, e.g., directional nipple 26, for providing connection to a vacuum or aspirating device, not shown. Distal connection 504 is provided with a hollow interior in which catheter 12 is received and sealed thereto by any convenient means, such as by adhesive or by being molded integrally with the leur lock. An outer sleeve, not shown, optionally is slid over and optionally secured to catheter 12 and distal connection 504 by adhesive or other convenient attaching means. A proximal connection, e.g., directional nipple 30 from FIG. 1, is also provided having a threaded portion 506. A grippable cap 36 is also provided which includes a hollowed cylindrical portion. The interior wall, not shown, of the hollowed cylindrical portion of grippable cap 36 is threaded to receive the threaded portion 506 of the proximal connection. Grippable cap 36 provides control over stylet 20 which is suitably connected to cap 36 by adhesive. Stylet 20 passes through the interior of directional nipple 30, through leur lock 24 and on through the connection 504. In one embodiment, shown in FIG. 5, the coupling member 234 described above which connects the second spring section 224 to the stylet 20 acts as a stop member 508. Alternatively, a stop member 508 is crimped about stylet 20 at any convenient portion thereof and is separate from the coupling member 234. In either embodiment, stop member 508 will cooperate with stop band 502 that is crimped about the catheter 12 and is positioned between stop member 508 and connection 504 to limit extreme retractable movement thereof.

While the invention has been described in connection with what is presently considered to be the most practical and preferred embodiment, it is to be understood that the present invention is not limited to the disclosed embodiment, but, to the contrary, it is intended to cover various modifications and equivalent arrangements included within the spirit and scope of the appended claims.

The invention claimed is:

1. A medical device, comprising:
   a flexible outer tubular member having proximal and distal ends;
   a flexible inner member slidably received within the flexible outer tubular member, the flexible inner member comprising a stylet adjacent the proximal end of the outer tubular member, a first spring section having proximal and distal ends and being oriented adjacent the distal end of the outer tubular member, and a second spring section coupled to the stylet and the proximal end of the first spring section so that the stylet extends through the second spring section and partially into the proximal end of the first spring section; and
   a hollow needle member coupled to the distal end of the first spring section,
   wherein the device has a retracted position wherein the needle member is retractably housed within the outer tubular member and a distal end of the device is flexible, a first position wherein the needle member is deployed beyond the distal end of the outer tubular member and the second spring section is in an uncompressed state, and a second position wherein the second spring section is in a compressed state.

2. The device of claim 1, further comprising:
a hard tip rigidly fixed to the distal end of the outer tubular member, the tip including a bearing surface on the proximal end thereof.

3. The device of claim 2, wherein the needle member includes a limiting member rigidly secured at a point along the length of the needle member and contacting the bearing surface of the tip member in the first and second positions.

4. The device of claim 2, further comprising:
a locking member securing the inner member into a contacting relationship with the bearing surface to prevent retractable movement of the needle member when in the second position.

5. The device of claim 1, wherein the first spring section comprises a first wavelength and the second spring section comprises a second wavelength greater than the first wavelength in the retracted and first positions.

6. The device of claim 5, wherein the second spring section comprises a third wavelength in the second position, the third wavelength being less than the second wavelength.

7. The device of claim 1, further including a stop member positioned within the flexible outer tubular member to control the amount of refraction of the needle member.

8. The device of claim 7, wherein the stop member comprises a crimped band.

9. The device of claim 1, wherein the second spring section forms an inner volume and the stylet occupies a portion of that inner volume.

10. The device of claim 1, wherein the stylet extends into the hollow needle in the second position.

11. The device of claim 1, wherein the first spring section forms an inner volume and the stylet passes through the inner volume in the second position.

12. The device of claim 11, wherein the stylet extends into the needle member in the second position.

13. A tissue collection device, comprising:
an elongated outer flexible hollow catheter having proximal and distal ends;
an elongated member having proximal and distal ends and being slidably positioned within the hollow catheter and defining an axis along its length;
a helically wound wire member having proximal and distal ends and having its proximal end coaxially attached to the elongated member adjacent the distal end thereof, wherein the helically wound wire member has a proximal region having a first wavelength, and a distal region having a second wavelength normally smaller than the first wavelength with the distal end of the elongated member extending through the proximal region and partially into the distal region when the elongated member is in a retracted condition; and
a sampling member attached to the distal end of the helically wound wire member.

14. The device of claim 13, wherein the sampling member comprises a hollow needle.

15. The device of claim 14, wherein the device has a first extended position wherein the sampling member extends beyond the distal end of the hollow catheter.

16. The device of claim 15, wherein the device his a second extended position wherein the sampling member extends beyond the distal end of the hollow catheter and the proximal region has a compressed wavelength shorter than the first wavelength.

17. The device of claim 16, further comprising:
a hard tip rigidly fixed to the distal end of the hollow catheter, the tip including a bearing surface on the proximal end thereof.

18. The device of claim 17, wherein the sampling member includes a limiting member rigidly associated therewith so that the limiting member contacts the bearing surface in the second extended position.

19. The device of claim 13, wherein the device has a retracted position in which the sampling member is housed within the hollow catheter.

20. The device of claim 13, wherein the device has a first extended position wherein the sampling member extends beyond the distal end of the hollow catheter and the distal end of the device has a first level of flexibility, and a second extended position wherein the proximal region has a compressed wavelength shorter than the first wavelength and the distal end of the device has a second level of flexibility that is more rigid than the first level of flexibility.

21. The device of claim 20, wherein the elongated member extends into the sampling member in the second extended position.

* * * * *